United States Patent [19]
Morii et al.

[11] Patent Number: 4,985,362
[45] Date of Patent: Jan. 15, 1991

[54] PROCESS OF PURIFYING TPA

[75] Inventors: Mitsuyoshi Morii; Masaharu Ohoka, both of Yokohama; Toshihiko Suzuki, Tokyo; Katsuyuki Suzuki, Hiroshima; Nobuhiro Kawashima, Sagamihara; Noriko Morii; Kunizou Mori, both of Yokohama, all of Japan

[73] Assignee: Mitsui Toatsu Chemicals Incorporated, Tokyo, Japan

[21] Appl. No.: 97,678

[22] Filed: Sep. 17, 1987

[30] Foreign Application Priority Data

Sep. 22, 1986 [JP] Japan .................. 61-222111

[51] Int. Cl.$^5$ .................... C12N 9/64; C12N 9/50
[52] U.S. Cl. ..................... 435/226; 435/212; 435/219; 435/815
[58] Field of Search ............. 435/212, 226, 215, 217, 435/183, 219, 814, 815

[56] References Cited

U.S. PATENT DOCUMENTS 4,552,760 11/1985 Murakami et al. ............. 435/215 X
4,568,544 2/1986 Hasegawa et al. ............. 435/215 X

FOREIGN PATENT DOCUMENTS

EP124613 11/1984 European Pat. Off. ......... 424/94.64
EP0163751 12/1985 European Pat. Off. .
8701389 3/1987 World Int. Prop. O. .......... 435/212

OTHER PUBLICATIONS

Rijken, D. et al., J. Biol. Chem., vol. 256, pp. 7035–7041, 1981.
Pharmacia-Ion Exchange Chromatography, Principles & Methods, pp. 18–22, 1980.
"Human Tissue-Type Plasmsnogen Activator", Kruithof et al; Biochem. J., (1985).
Pharmacia-Ion Exchange Chromatography, Principles & Methods, pp. 29–38, 1983.

Primary Examiner—David M. Naff
Assistant Examiner—Charles L. Patterson, Jr.
Attorney, Agent, or Firm—Nixon & Vanderhye

[57] ABSTRACT

Tissue plasminogen activator (tPA) species having a molecular weight of about 70,000 daltons is isolated in a purified form from a crude tPA preparation containing various tPA species having different molecular weights by bringing the crude tPA preparation into contact with a cation exchanger in advance and separating the desired tPA species selectively from the cation exchanger by means of the salt gradient elution method.

2 Claims, No Drawings

PROCESS OF PURIFYING TPA

BACKGROUND OF THE INVENTION

1. Field of the Invention

This invention relates to a process for the purification of tissue plasminogen activator (tPA).

More particularly, it relates to a process for the purification of tPA which comprises bringing a crude tPA preparation containing various tPA species of different molecular weights into contact with a cation exchanger in advance and separating tPA having a molecular weight of about 70,000 daltons selectively from the cation exchanger by means of the salt gradient elution method.

2. Description of the Prior Art

No practical processes have yet been known to refine tPA having a desired molecular weight from a culture medium which has cultured tPA-producing cells and thus contained a crude tPA preparation with various tPA species of different molecular weights.

As processes to separate proteins having different molecular weights, it has been known that the gel-filtration process is generally applicable and that cation exchangers are used for the purification of tPA (Japanese Patent Laid Open No. 174727/1985). However, no purification processes have been known at all, which purify and prepare a tPA species of a desired molecular weight by removing other tPA species than that having the particular molecular weight, for example, about 70,000 daltons as in the process of the present invention.

SUMMARY OF THE INVENTION

An object of the present invention is to prepare tPA having a molecular weight of about 70,000 daltons selectively from proteins which react with an anti-human tPA antibody and have different molecular weights.

When tPA-producing cells are cultured to obtain tPA, the resulting culture broth contains, as proteins reactive with an anti-human tPA antibody, various tPA species including tPA species having molecular weights of from 30,000 to 45,000 daltons, tPA species having molecular weights of from 50,000 to 80,000 daltons and tPA species having a molecular weight of 100,000 daltons or higher. The present invention provide a process for isolating and purifying tPA with a molecular weight of about 70,000 daltons from a solution containing those various tPA species of different molecular weights and other proteinaceous impurities.

The present inventors have studied the reaction between tPA species of different molecular weights and a cation exchanger with a view to solving the above problems. As a result, it was found that the tPA species of different molecular weights had individually different binding strengths to the cation exchanger. Utilization of this property has led to completion of a process for preparing tPA with a molecular weight of about 70,000 daltons from various tPA species of different molecular weights.

Namely, the above object has been accomplished by a purification process of tPA which (a) comprises bringing a crude tPA preparation containing, as impurities, proteins which react with an anti-human tPA antibody and have molecular weights other than about 70,000 daltons into intimate contact with a cation exchanger in advance and (b) separating tPA having a molecular weight of about 70,000 daltons selectively from the cation exchanger by means of the salt gradient elution method.

DETAILED DESCRIPTION OF THE INVENTION

In the process of the present invention, tissue plasminogen activator (tPA) is produced in the tissue of a higher animal, and is a protein which activates plasminogen, a precursor of plasmin which is a proteolytic enzyme specific to fibrin.

When tPA-producing cells are cultured to obtain tPA, the culture medium contains various tPA species of different molecular weights such as those having molecular weights of from 30,000 to 45,000 daltons, those having molecular weights of from 50,000 to 80,000 daltons and that having a molecular weight of 100,000 daltons or higher as proteins reactive with an anti-human tPA antibody. These tPA species include tPA, active degraded products of tPA, polymers of tPA, complexes of tPA and other protein and the like.

The culture medium containing the tPA to be purified according to the process of the present invention may include a culture medium of human melanoma cells, culture medium of normal human cells and culture medium of cells carrying the human tPA gene integrated according to the DNA recombinant technique. Culture media formed by partially refining the aforesaid media may also be used.

As illustrative functional groups of the cation exchanger useful in the practice of the process of the present invention may be mentioned a carboxymethyl, phospho and sulfopropyl group, while the carrier may include agarose, cellulose and polyacrylamide granules and also a combination thereof.

In the process of the present invention, a solution containing various tPA species of different molecular weights and other proteinaceous impurities is first adjusted to be weakly acidic for the purpose of allowing them to be adsorbed onto a cation exchanger.

The cation exchanger brought into contact with the solution adsorbs practically all of the tPA species of different molecular weights.

After washing the cation exchanger as required, tPA of about 70,000 daltons in molecular weight is allowed to elute selectively at a pH in a specific pH range by means of, what is called, the salt gradient elution method, in which elution is effected by varying the salt concentration of an eluent that is nearly neutral or has generally a pH in the range of 6.0–7.5, so that the desired tPA can be separated and purified.

Sodium chloride, potassium chloride, sodium phosphate and potassium phosphate are generally used as the salt in most cases. However, the salt to be used is not particularly limited to these compounds. Further, as regards the concentration of the salt, a range of concentration, at which tPA can be eluted, should be applied in accordance with the kind of the functional group of the cation exchanger to be used and the kind of the resin.

Further, the applicable salt gradient elution method may include, for example, the linear gradient or stepwise method.

EXAMPLE 1

After culturing Bowes melanoma cells (ATCC CRL1424 G361) in RPMI-1640 culture medium supplemented with 10% of thermoinactivated (56° C., 30 minutes) fetal calf serum, the cultured cells were washed once. The washed cells were then cultured for 24 hours in a serum-free medium and the resultant culture supernatant was collected.

Phosphoric acid was added to 2 l of the culture supernatant. The collected supernatant was adjusted at a pH of 5.0 by adding phosphoric acid to 2 l of the supernatant, and then allowed to pass through a column containing 10 ml of CM-Sepharose (Pharmacia AB) equilibrated with a 0.05M sodium dihydrogenphosphate solution (pH 5.0) containing 0.15M of sodium chloride.

The column effluent was collected and its plasminogen-dependent fibrinolytic activity was measured. No activity was however detected.

After the whole culture supernatant had been passed through the column, the column was washed with a 25 mM phosphate buffer (pH 6.4) containing 0.1M of sodium chloride.

About 5% of the activity charged into the column was detected in the resulting solution. This solution was subjected to electrophoresis in an SDS polyacrylamide gel and was then analyzed by a zymography. A band corresponding to about 30,000 daltons in molecular weight was observed on the zymograph.

The adsorbed proteins were eluted with a 25 mM phosphate buffer (pH 6.0) by varying its sodium chloride concentration from 0.1M to 0.6M by means of the linear gradient method.

The eluate thus obtained exhibited a single band corresponding to a molecular weight of about 70,000 daltons on the zymograph in the range of 0.2M–0.35M in sodium chloride concentration. About 70% of the activity charged into the column was found to be recovered as the activity of this fraction.

EXAMPLE 2

Through a column containing 20 ml of an antihuman tPA antibody was passed 2 l of a culture supernatant prepared from the culture of human fetal lung cells (ATCC MRC-5 CCL-171) in a culture medium containing 10% of thermoinactivated (56° C., 30 minutes) fetal calf serum and 20 KIU/ml of aprotinin.

The effluent was collected and its plasminogen-dependent fibrinolytic activity was measured. This fraction exhibited an activity about 40% of the activity charged into the column. This activity was however concluded to be ascribable to urokinase because an anti-human urokinase antibody suppressed it completely.

The adsorbed proteins were washed with a 0.05M phosphate buffer (pH 7.5) containing 1.0M of sodium chloride and then eluted with a 0.05M phosphate buffer (pH 7.5) containing 2.0M of potassium thiocyanate.

The activity of the eluate was about 50% of the activity charged into the column. This eluted fraction was subjected to electrophoresis in an SDS polyacrylamide gel and then analyzed by a zymography. A large number of bands were detected in the range corresponding to about 30,000–150,000 daltons in molecular weight. These bands were concluded to be those of tPA because these bands were not detected when a fibrin-agar plate treated with an anti-human tPA antibody was used.

The solution was added with ammonium sulfate at a rate of 300 g/l, adjusted at a pH of 7.0 and then allowed to stand at 4° C. overnight.

The resulting precipitate was collected by centrifugation and dialyzed against a 25 mM phosphate buffer (pH 6.0) containing 0.1M of sodium chloride. The dialyzed solution was charged into a column containing 5 ml of sulfopropyl (SP) Sepharose (Pharmacia AB) equilibrated with a 25 mM phosphate buffer (pH 6.0) containing 0.1M of sodium chloride.

After the whole solution had been passed through the column, the column was washed with a 25 mM phosphate buffer (pH 6.0) containing 0.3M of sodium chloride. The effluent was collected and its plasminogen-dependent fibrinolytic activity was measured. It was found to be about 7% of the activity charged into the column. Bands were observed in the range corresponding to 30,000–60,000 daltons in molecular weight on a zymograph.

The proteins adsorbed onto the column were eluted with a 25 mM phosphate buffer (pH 6.0) containing 0.5M of sodium chloride. The eluate exhibited an activity about 80% of the activity charged into the column. A band corresponding to about 70,000 daltons in molecular weight was observed on a zymograph.

EXAMPLE 3

Through a column containing 50 ml of an antihuman tPA antibody was passed 2 l of a culture supernatant prepared from the culture of Chinese hamster ovary (CHO) cells with human tPA gene integrated therein (Dr. Chasin, Department of Biological Science, Columbia University) in a medium containing 10% of thermoinactivated (56° C., 30 minutes) fetal calf serum and 40 KIU/ml of aprotinin. The column was washed with a 0.05M phosphate buffer (pH 7.5) containing 1.0M sodium chloride and then the adsorbed proteins were eluted with a 0.1M glycine-HCl buffer (pH 3.5) containing 2.0M of ammonium thiocyanate.

The eluate was collected and its plasminogen-dependent fibrinolytic activity was measured. It was found to be about 95% of the activity charged into the column.

This eluted fraction was analyzed by a zymography after subjecting same to electrophoresis in an SDS polyacrylamide gel. Bands were observed in the range corresponding to 30,000–150,000 daltons in molecular weight on the zymograph.

This solution was added with ammonium sulfate at a rate of 300 g/l, adjusted in pH at 7.0 and allowed to stand at 4° C. overnight.

The resulting precipitate was collected by centrifugation and dialyzed against a 0.05M phosphate buffer (pH 6.0). This dialyzed solution was passed through a column containing CM-trisacryl M (LKB Co.) equilibrated with a 0.05M phosphate buffer (pH 6.0). The column was washed with the same buffer as used in the equilibration and the plasminogen-dependent fibrinolytic activity of the effluent was measured.

About 5% of the activity charged into the column was found to be recovered and bands were observed in the range corresponding to about 30,000–60,000 daltons in molecular weight on a zymograph.

The adsorbed proteins were eluted with a 0.05M phosphate buffer (pH 6.0) containing 0.15M of sodium chloride. The eluate exhibited an activity about 85% of the activity charged into the column. A band corresponding to about 70,000 daltons in molecular weight was recognized on a zymograph.

EXAMPLE 4

Two liters of a culture supernatant prepared from the culture of mouse fibroblast cells (Mouse C1271 ATCC CRL 1616) transformed by the human tPA gene in a culture medium containing 2% of thermoinactivated (56° C., 30 minutes) fetal calf serum and 40 KIU/ml of aprotinin were adjusted in pH at 4.5 with phosphoric acid and then passed through a column containing 10 ml of carboxymethyl (CM) Sepharose (Pharmacia AB) equilibrated with 0.05M sodium dihydrogenphosphate solution (pH 4.5) containing 0.15M of sodium chloride.

The resin containing the proteins adsorbed was washed with a 25 mM phosphate buffer (pH 6.4) containing 50 mM of sodium chloride and thereafter the proteins were eluted with a 50 mM phosphate buffer (pH 6.4) containing 0.5M of sodium chloride.

The plasminogen-dependent fibrinolytic activity of the eluate was measured. It was found to be about 90% of the activity charged into the column. This eluted fraction was subjected to electrophoresis in an SDS polyacrylamide gel and then analyzed by a zymography. Bands were observed as those of tPA in the range corresponding to 30,000–150,000 daltons in molecular weight on the zymograph.

This fraction was diluted tenfold with a 25 mM phosphate buffer (pH 6.0) and adjusted at a pH of 6.0. The resulting solution was allowed to flow through a column containing CM-trisacryl M equilibrated with a 25 mM phosphate buffer (pH 6.0) containing 0.05M of sodium chloride. The column was washed with the same buffer as used for the equilibration and the plasmincgen-dependent fibrinolytic activity of the effluent was measured. About 5% of the activity charged into the column was found to be recovered and bands were observed in the range corresponding to about 30,000–60,000 daltons in molecular weight on a zymograph.

The proteins adsorbed were eluted with a 0.05M phosphate buffer (pH 6.4) containing 0.1M of sodium chloride. The activity of the eluate was about 85% of the activity charged into the column. tPA contained in this fraction was confirmed as a band corresponding to about 70,000 daltons in molecular weight on a zymograph.

EXAMPLE 5

Ammonium sulfate was added at a rate of 300 g/l to 2 l of a culture supernatant prepared from the culture of human fetal amniotic cells (FL ATCC CCL-62) carrying the human tPA gene associated with human cytomegalovirus (HCMV) as a promoter for human tPA expression in a culture medium containing 2% of thermoinactivated (56° C., 30 minutes) fetal calf serum and 20 KIU/ml of aprotinin. The resulting solution was adjusted at a pH of 7.0 and then allowed to stand at 4° C. overnight.

The thus-formed precipitate was collected by centrifugation and dissolved in a 0.04M phosphate buffer (pH 7.5), followed by dialysis against this buffer for desalting. This solution was allowed to pass through a column containing 10 ml of hydroxyapatite equilibrated with a 0.04M phosphate buffer (pH 7.5). After the whole solution had been passed through the column, the column was washed with the same buffer as used in the equilibration.

Measurement of the plasminogen-dependent fibrinolytic activity of the effluent revealed that it was about 5% of the activity charged into the column. This fraction was subjected to electrophoresis in an SDS polyacrylamide gel and analyzed by a zymography. This effluent exhibited bands in the range corresponding to about 30,000 to 60,000 daltons in molecular weight on the zymograph.

The proteins adsorbed was eluted with a 0.3M phosphate buffer (pH 6.0). The eluate exhibited an activity about 85% of the activity charged into the column, and bands corresponding to about 70,000 daltons and 100,000 daltons or higher in molecular weight were observed on a zymograph.

This fraction was diluted sixfold with water and adjusted in pH at 5.5 with phosphoric acid. The resulting solution was passed through a column of CM-Sepharose equilibrated with a 0.05M phosphate buffer (pH 5.5).

After the whole solution had been passed through the column, the adsorbed proteins were eluted with a 25 mM phosphate buffer (pH 6.4) containing 0.15M of sodium chloride.

The recovered activity of the eluate was about 80% of the activity charged into the column. A band corresponding to a molecular weight of about 70,000 daltons was recognized on a zymograph.

The remaining adsorbed proteins were eluted with a 25 mM phosphate buffer (pH 6.4) containing 0.5M of sodium chloride. The eluate exhibited a tPA activity about 15% of the total activity charged into the column. It gave bands corresponding to molecular weights of 70,000 daltons and 100,000 daltons or higher on a zymograph.

EXAMPLE 6

Ammonium sulfate was added at a rate of 300 g/l to 2 l of a culture supernatant prepared from the culture of mouse myeloma cells (P3×63 Ag8 ATCC TIB-9) carrying the human tPA gene associated with immunoglobulin G as a promoter for human tPA expression in a culture medium containing 2% of thermoinactivated (56° C., 30 minutes) fetal calf cerum and 20 KIU/ml of aprotinin. The resulting solution was adjusted at a pH of 7.0 and allowed to stand at 4° C. overnight.

The resulting precipitate was collected by centrifugation and dissolved in 25 mM Tris-HCl buffer (pH 8.0), followed by dialysis against the buffer for desalting.

The solution was allowed to flow through a column of DEAE-Sepharose (Pharmacia AB) equilibrated with a 25 mM Tris-HCl buffer (pH 8.0).

After the whole solution had been passed through the column, the column was washed with the same buffer as used in the equilibration. The plasminogen-dependent fibrinolytic activity of the effluent and eluate was about 5% of the activity charged into the column. The adsorbed proteins were eluted with a 25 mM Tris-HCl buffer (pH 8.0) containing 0.3M of sodium chloride.

The activity of the eluate was about 90% of the activity charged into the column. The eluate was subjected to electrophoresis in an SDS acrylamide gel and analyzed by a zymography. Bands as tPA were observed in the range corresponding to about 30,000–150,000 daltons in molecular weight on the zymograph.

This fraction was adjusted in pH at 6.0 and diluted threefold with a 25 mM phosphate buffer (pH 6.0). The resulting solution was passed through a column of CM-Sepharose (Pharmacia AB) equilibrated with a 25 mM phosphate buffer (pH 6.0) containing 0.10M of sodium chloride.

After the whole solution had been passed through the column, the column was washed with a 25 mM phosphate buffer (pH 6.0) containing 0.1M of sodium chloride. In this way, about 5% of the activity charged into the column was detected. The effluent and eluate were subjected to electrophoresis in an SDS-polyacrylamide gel and analyzed by a zymography. Bands were observed in the range corresponding to about 30,000–60,000 daltons in molecular weight on the zymograph.

The adsorbed proteins were eluted with a 25 mM phosphate buffer (pH 6.0) containing 0.3M of sodium chloride.

The activity of the eluate was about 80% of the activity charged into the column. A single band corresponding to about 70,000 daltons in molecular weight was observed on the zymograph.

Subsequently, the column was subjected to elution with a 25 mM phosphate buffer (pH 6.0) containing 0.6M of sodium chloride. Then, it was found that about 15% of the activity charged into the column was recovered and bands corresponding to 70,000 daltons and 100,000 daltons or higher in molecular weight were observed on a zymograph.

EXAMPLE 7

Host yeast cells transformed with the human tPA gene therein were allowed to grow in a standard yeast culture medium to which was applied generally the method described in Principles and Practice of Recombinant DNA Research with Yeast in the Molecular Biology of Yeast Saccharomyces: Metabolism and Gene Expression, pp. 603–636, Cold Spring Harbor Laboratory, Cold Spring Harbor, N.Y. (1982).

The resultant cells were ground with glass beads. tPA was extracted with a 0.04M phosphate buffer (pH 7.5) containing 0.02% of Tween 80 and 20 KIU/ml of aprotinin. The extract was centrifuged to obtain a supernatant. From this supernatant, tPA was recovered in the same manner as in Example 1. The recovery rate of the tPA was about 60% and its molecular weight was about 70,000 daltons.

What is claimed is:

1. A process for purifying tPA comprising the steps:
   (a) contacting a carboxymethyl agarose exchange resin with a crude tPA preparation containing tPA having a molecular weight of about 70,000 daltons, together with impure tPA species including active degraded products of tPA, polymers of tPA, and complexes of tPA with other proteins, said impure tPA species having molecular weights other than about 70,000 daltons and capable of reacting with an anti-human tPA antibody;
   (b) treating said exchange resin with an eluant having a salt concentration of less than 0.15M and a pH in the range of 6.0–6.4 to elute the impure tPA species having molecular weights of less than about 70,000 daltons; and thereafter
   (c) treating said exchange resin with an eluant having a salt concentration in the range of 0.175–0.375M and a pH in the range of 6.0–6.4 to elute the tPA having a molecular weight of about 70,000 daltons and recovering the resultant eluate.

2. A process for purifying tPA comprising the steps of:
   (a) contacting a carboxymethyl acrylamide copolymer exchange resin with a crude tPA preparation containing tPA having a molecular weight of about 70,000 daltons, together with impure tPA species including active degraded products of tPA, polymers of tPA, and complexes of tPA with other proteins, said impure tPA species having molecular weights other than about 70,000 daltons and capable of reacting with an anti-human tPA antibody;
   (b) treating said exchange resin with an eluant having a salt concentration of at most 0.075M and a pH in the range of 6.0–6.4 to elute the impure tPA species having molecular weights of less than about 70,000 daltons; and thereafter
   (c) treating said exchange resin with an eluant having a salt concentration of 150 mM–200 mM, and a pH in the range of 6.0–6.4 to elute said tPA having a molecular weight of about 70,000 daltons and recovering the resulting eluate.

* * * * *